United States Patent [19]

Triantafillou et al.

[11] Patent Number: 5,659,102
[45] Date of Patent: Aug. 19, 1997

[54] PRODUCTION OF ISO OLEFIN OLIGOMERS

[75] Inventors: Nicholas D. Triantafillou, Bryn Mawr; Shaw-Chan Lin; Daniel M. Trauth, both of West Chester, all of Pa.

[73] Assignee: ARCO Chemical Technology L.P., Greenville, Del.

[21] Appl. No.: 627,746

[22] Filed: Apr. 2, 1996

[51] Int. Cl.$^6$ ............................................. C07C 1/24
[52] U.S. Cl. ................................... 585/639; 585/640
[58] Field of Search ....................................... 585/639

[56] References Cited

U.S. PATENT DOCUMENTS

| | | | |
|---|---|---|---|
| 3,510,538 | 5/1970 | Rosenthal | 585/639 |
| 3,665,048 | 5/1972 | Grane et al. | 585/640 |
| 3,847,996 | 11/1974 | Caserio et al. | 585/639 |
| 4,065,512 | 12/1977 | Cares | 585/639 |
| 4,155,945 | 5/1979 | Levine | 585/639 |
| 4,873,391 | 10/1989 | Inoue et al. | 585/639 |
| 5,157,192 | 10/1992 | Sorensen | 585/640 |
| 5,436,382 | 7/1995 | Gupta | 585/639 |
| 5,475,183 | 12/1995 | Araki et al. | 585/640 |

FOREIGN PATENT DOCUMENTS

| | | | |
|---|---|---|---|
| 023119 | 1/1981 | European Pat. Off. | 585/639 |
| 104376 | 6/1984 | Japan | 585/639 |

*Primary Examiner*—Ellen M. McAvoy
*Attorney, Agent, or Firm*—William C. Long

[57] ABSTRACT

A tertiary alkanol such as tertiary butyl alcohol is converted in one step to an oligomer of the olefin corresponding to the alkanol by reacting a homogeneous solution of the alkanol and an acid catalyst at conditions effective to form the oligomer.

8 Claims, 1 Drawing Sheet

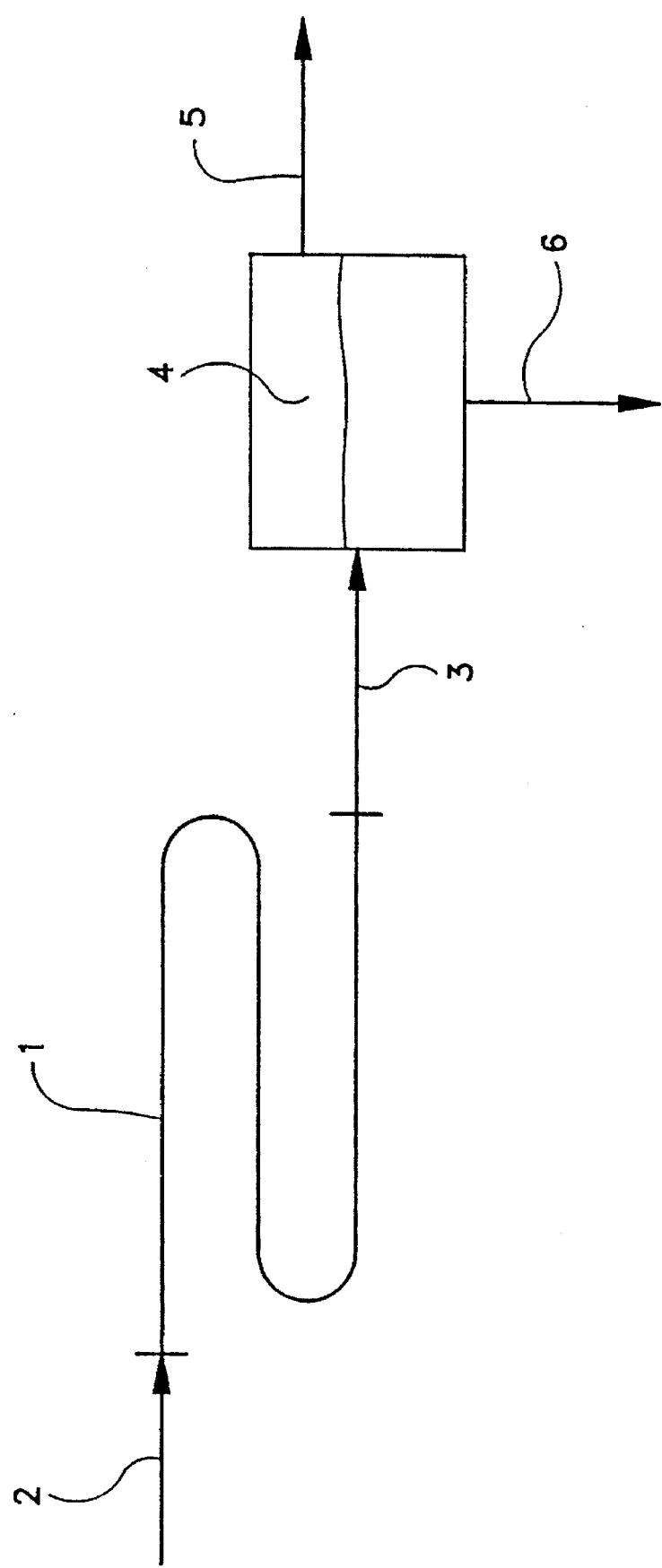

PRODUCTION OF ISO OLEFIN OLIGOMERS

BACKGROUND OF THE INVENTION

1. Field of the Invention

The present invention relates to the conversion of tertiary alkanols such as tertiary butyl alcohol to oligomers of the corresponding iso-olefin in a one-step liquid phase process using a homogeneous catalyst such as methane sulfonic acid.

2. Description of the Prior Art

The dehydration of tertiary alkanols such as tertiary butyl alcohol to the corresponding olefin is a well known reaction. See, for example, U.S. Pat. Nos. 5,475,183, 3,665,048, and the like. Catalysts such as alumina, methane sulfonic acid, and the like have been used.

Further, it is known that tertiary alkanols such as tertiary butyl alcohol can be directly converted to oligomers of the corresponding iso-olefin in one step using solid heterogenous catalysts such as zeolite Beta. See U.S. Pat. No. 5,157,192.

There are, however, problems associated with the heterogeneous catalyst systems. Product separation is a problem as is control of the reaction and the removal of heat in heterogeneous systems. In addition, condensation products tend to accumulate on the solid catalyst surfaces leading to a rapid decline in catalyst activity and the necessity for frequent reactivation.

SUMMARY OF THE INVENTION

In accordance with the present invention, a tertiary alkanol is contacted in the liquid phase with a homogeneous acid catalyst at conditions effective for the selective formation of dimers and trimers of the olefin corresponding to the tertiary alkanol. In especially preferred practice, tertiary butyl alcohol is converted in high yield and selectivity to diisobutylene and triisobutylene through practice of the invention.

BRIEF DESCRIPTION OF THE DRAWING

The accompanying drawing is a schematic illustration of practice of the invention.

DETAILED DESCRIPTION

Tertiary alkanols which are reacted in accordance with the invention preferably are tertiary butyl alcohol and tertiary amyl alcohol; other tertiary alkanols can be reacted.

The tertiary alcohol conversion is carried at conditions effective to convert at least about 50% of the tertiary alkanol, preferably 60 to 98% to dimers and trimers corresponding to the olefin derivative of the alkanol. Pressures employed are sufficient to maintain the liquid phase, illustrative pressures are 20 to 200 psia, preferably 40 to 100 psia.

Reaction temperatures are effective to achieve the above indicated conversions of tertiary alkanol to the dimer and trimer of the corresponding olefin. Suitable temperatures range from 50° to 150° C., preferably 60 ° to 90 ° C.

Reaction times range from about 30 to 120 minutes, preferably 60 to 100 minutes.

The use of a homogeneous acid catalyst is essential to practice of the invention. Organic sulfonic acids are preferred. Methane sulfonic acid and para toluene sulfonic acid are especially useful. Other less preferred acid catalysts include sulfuric acid, phosphoric acid, and the like.

The catalyst is used in amount ranging from about 10 to 60 wt % preferably 30 to 50 wt %, based on total feed.

Referring to the drawing, the conversion of tertiary butyl alcohol is illustrated. A homogeneous solution of tertiary butyl alcohol and catalyst is fed to reaction zone 1 via line 2. Reaction zone 1 preferably comprises an isothermal pipe reactor or other plug flow system. As the feed mixture passes through the reactor, reaction conditions are maintained to ensure the reaction mixture is in the liquid phase and to provide for the desired reaction. Tertiary butyl alcohol is converted to diisobutylene and triisobutylene, and the reaction mixture becomes a two phase liquid mixture. The reaction mixture exits reaction zone 1 via line 3 and passes to zone 4 wherein it is separated into an upper hydrocarbon phase comprised of diisobutylene and triisobutylene, and a lower polar phase comprised of unreacted tertiary butyl alcohol, water and catalyst.

The hydrocarbon phase is removed via line 5, and the various components can be readily recovered by distillation (not shown).

The polar phase is removed via line 6 and after purging water and other impurities (not shown) the tertiary butyl alcohol and catalyst values can be recycled to reaction zone 1.

EXAMPLE

A tertiary butanol feed (94% tertiary butyl alcohol) was admixed with methane sulfonic acid and fed to an isothermal pipe reactor. The weight ratio of tertiary butyl alcohol/methane sulfonic acid was 60/40. Residence time in the reactor was 1.6 hours and reaction conditions were 80° C. and 60 psig.

The reaction mixture was separated into an organic phase which contained less than 1% tertiary butyl alcohol and a polar phase which contained essentially no isobutylene or oligomers.

Tertiary butyl alcohol conversion was 92% with 7% selectivity to isobutylene, 57% selectivity to diisobutylene, 33% selectivity to triisobutylene and 2% selectivity to tetraisobutylene. On an isobutylene free basis, the combined $C_8$ plus $C_{12}$ selectivity was nearly 98%.

We claim:

1. The process for converting a tertiary alkanol to an oligomer of the olefin corresponding to the said alkanol which comprises reacting a homogeneous solution consisting essentially of the tertiary alkanol and an acid catalyst in the liquid phase at conditions effective to form said oligomer, and phase separating the resulting liquid reaction mixture into an upper oligomer containing phase and a lower aqueous polar phase.

2. The process of claim 1 wherein the alkanol is tertiary butanol and isobutylene oligomers are formed.

3. The process of claim 1 wherein the alkanol is tertiary amyl alcohol and isoamylene oligomers are formed.

4. The process of claim 1 wherein the acid catalyst is an organic sulfonic acid.

5. The process of claim 1 wherein the acid catalyst is methane sulfonic acid.

6. The process of claim 1 wherein the acid catalyst is para toluene sulfonic acid.

7. The process of claim 1 wherein the acid catalyst is sulfuric acid.

8. The process of claim 1 wherein the acid catalyst amount is 10 to 60 wt % based on total feed to the reaction.

* * * * *